（12）United States Patent
Caraffi et al.

(10) Patent No.: US 9,498,125 B2
(45) Date of Patent: Nov. 22, 2016

(54) METHOD FOR OPERATING AN EYE TRACKING DEVICE AND EYE TRACKING DEVICE FOR PROVIDING AN ACTIVE ILLUMINATION CONTROL FOR IMPROVED EYE TRACKING ROBUSTNESS

(71) Applicant: SENSOMOTORIC INSTRUMENTS GESELLSCHAFT FUR INNOVATIVE SENSORIK MBH, Teltow (DE)

(72) Inventors: Claudio Caraffi, Berlin (DE); Matthias Nieser, Berlin (DE); Fabian Wanner, Berlin (DE); Walter Nistico, Berlin (DE)

(73) Assignee: SENSOMOTORIC INSTRUMENTS GESELLSCHAFT FUR INNOVATIVE SENSORIK MBH, Teltow (DE)

( * ) Notice: Subject to any disclaimer, the term of this patent is extended or adjusted under 35 U.S.C. 154(b) by 0 days.

(21) Appl. No.: 15/034,898

(22) PCT Filed: Dec. 9, 2014

(86) PCT No.: PCT/EP2014/077081
§ 371 (c)(1),
(2) Date: May 6, 2016

(87) PCT Pub. No.: WO2015/086617
PCT Pub. Date: Jun. 18, 2015

(65) Prior Publication Data
US 2016/0270655 A1 Sep. 22, 2016

(30) Foreign Application Priority Data
Dec. 9, 2013 (EP) ..................................... 13196288

(51) Int. Cl.
*A61B 3/14* (2006.01)
*A61B 3/113* (2006.01)
*A61B 3/00* (2006.01)
*A61B 3/15* (2006.01)
*A61B 3/18* (2006.01)

(52) U.S. Cl.
CPC ............. *A61B 3/113* (2013.01); *A61B 3/0008* (2013.01); *A61B 3/0025* (2013.01); *A61B 3/158* (2013.01); *A61B 3/18* (2013.01); *A61B 2562/0219* (2013.01); *A61B 2562/0223* (2013.01)

(58) Field of Classification Search
CPC .......... A61B 3/112; A61B 3/113; A61B 3/14
USPC ......................... 351/209, 210, 246, 205, 200
See application file for complete search history.

(56) References Cited

U.S. PATENT DOCUMENTS

| 5,481,622 A | 1/1996 | Gerhardt et al. |
| 8,529,063 B2 * | 9/2013 | Bonnin .................. A61B 3/113 351/209 |
| 2013/0016320 A1 | 1/2013 | Naba |

FOREIGN PATENT DOCUMENTS

| WO | 00/26713 A1 | 5/2000 |
| WO | 03/017203 A1 | 2/2003 |

OTHER PUBLICATIONS

International Search Report of PCT/EP2014/077081 dated Mar. 5, 2015 [PCT/ISA/210].
Written Opinion of PCT/EP2014/077081 dated Mar. 5, 2015 [PCT/ISA/237].

* cited by examiner

*Primary Examiner* — Hung Dang
(74) *Attorney, Agent, or Firm* — Sughrue Mion, PLLC (57) ABSTRACT

The invention relates to an eye tracking device and a method for operating an eye tracking device (30) comprising an imaging device (32), a plurality of light sources (34), a processing unit and a control unit. The imaging device (32) captures a first image (36a) while at least one of the light sources (34) emits light. If at least one first reflection (14; 16; 16a-16f) is detected, a position in the first image (36a) of the at least one first reflection (14; 16; 16a-16f) is determined, the first reflection (14; 16; 16a-16f) is categorized on the basis of the position in the first image (36a) and if the first image (36a) does not fulfill a predefined quality criterion, the plurality of light sources (34) is controlled in dependence of the categorization by changing the light intensity of at least one light source (34).

29 Claims, 4 Drawing Sheets

METHOD FOR OPERATING AN EYE TRACKING DEVICE AND EYE TRACKING DEVICE FOR PROVIDING AN ACTIVE ILLUMINATION CONTROL FOR IMPROVED EYE TRACKING ROBUSTNESS

CROSS REFERENCE TO RELATED APPLICATIONS

This application is a National Stage of International Application No. PCT/EP2014/077081, filed Dec. 9, 2014, claiming priority based on European Patent Application No. 13 196 288.8, filed Dec. 9, 2013, the contents of all of which are incorporated herein by reference in their entirety.

DESCRIPTION

The present invention relates to a method for operating an eye-tracking device, especially a remote eye tracking device, for capturing at least one property of at least one eye of a user. The eye tracking device comprises at least one imaging device capable of capturing images of the eye of the user, a plurality of light sources capable of illuminating the eye of the user, a processing unit capable of processing images captured by the imaging device and a control unit capable of controlling the plurality of light sources in their light intensity separately. Furthermore, the capturing unit captures a first image while at least one of the light sources emits light and the processing unit processes the first image and by processing the first image the processing unit determines whether reflections are detected in the first image. The invention further relates to an eye tracking device, especially a remote eye tracking device, for capturing at least one property of at least one eye of a user.

This invention applies in the context of an eye tracking device, which is an apparatus to detect and track the position, orientation or other properties of the eyes of a user, like pupil dilation, intra-ocular distance, etc. A remote eye tracking device is an eye tracking device that is not mechanically contacted with a user, especially so that the user can move freely relative to the eye tracking device and its components like the imaging device and the illumination unit that comprises the plurality of light sources.

Eye tracking devices, especially remote eye tracking devices, known from the prior art usually use one imaging device and two infrared light sources, usually LEDs, to be able to find the eyes of a user in a capturing area and calculate the viewing direction of the eyes. This can be done for example through the detection of the iris or pupil center as well as the reflections, e.g. glints, of the light sources in the user's eyes. These features make it possible to estimate the gaze direction and thus the point the user is looking at.

Furthermore, current state of the art eye tracking systems use illuminations sources, which either are constantly on during the image acquisition or are pulsed during the exposure time window of the image sensor, which for all practical purposes achieves the same effect. Moreover, there are also known tracking systems from the prior art that can adjust the position or illumination intensity of illumination sources to enhance the tracking quality.

For example, from JP 2005 211 329 there is known an eye movement measuring device for measuring the movement of the eye ball, especially in the field of medical treatment and clinical diagnostics of dementia. This measuring device comprises a light source and a mirror, which can be adjusted in their positions, preferably so that the cornea-reflex optical image may approach a perfect circle. Unfortunately, such a method is not quite suitable for conventional eye tracking devices as the preconditions of a surgery situation is different. Usually, the patient has to sit still or to fixate a fix point during the measurement, while conventional eye tracking systems have to manage to track frequent and fast changes in the gaze direction of a user to provide real time eye tracking. Therefore, changing the position of a mirror or a light source in combination with eye tracking would take too long for achieving good tracking qualities.

Furthermore, WO 2013/117999 A1 describes a head-mounted gaze tracking system, wherein the intensity of light sources is modified based on a distance of the eye or the pupil from a substantially central position to achieve a better tracking quality. Similarly, the US 2013/0114850 A1 also describes a head-mounted gaze tracking system, which uses several light sources to achieve an overall illumination of the eyes. Disadvantageously, such head-mounted systems can't cope with problems of remote eye tracking as during remote eye tracking the user can change the position of his head relative to the eye tracking device and therefore relative to the light sources. As a consequence, remote eye tracking systems have to deal with much greater problems, like tracking under extreme tracking angles. Furthermore, situations can occur when the eye of the user is occluded for example by a hand of the user. Additionally it is especially problematic when the user wears prescription glasses or other sorts of visual aids, since these can produce extra reflections of the light sources that disturb eye tracking.

To deal with this problem, JP 2005 296383 proposes to use a plurality of light sources and if reflections of a user's spectacles are detected in an image the infrared irritation direction is switched in a predetermined order until no reflections from a user's spectacles are detected anymore. This procedure has the disadvantage that plenty of light sources are needed to increase the probability that at least one image can be obtained without spectacle reflections to an acceptable quantum, if at all. Therefore, one has to take a high risk of that only few images of a plenty of captured images can be used for eye tracking, which reduces the tracking quality enormously, and at the same time plenty of light sources are needed to get at least some useful images.

The object of the present invention is to provide a method for operating an eye tracking device and an eye tracking device as indicated in the preambles of the independent claims, which can increase the robustness of eye tracking, especially of remote eye tracking.

This object is solved by a method for operating an eye tracking device and an eye tracking device with the features of the independent claims.

According to the invention the capturing unit captures a first image when at least one of the light sources emits light and the processing unit processes the first image and by processing the first image, the processing unit determines whether reflections are detected in the first image. Furthermore, if at least one first reflection is detected, a position in the first image of the at least one reflection is determined and a first reflection is categorized at least on the basis of the position in the first image. If the first image does not fulfil a predefined quality criterion, the plurality of light sources are controlled at least independence of the categorization by changing the light intensity of at least one light source of the plurality of light sources.

The present invention is based on the finding that not each reflection that might not be useful for capturing a property of an eye at first sight, like reflections from spectacles, is at the same time disruptive and prevents the eye tracking device from capturing the at least one property of the eye. As advantageously according to the invention the position of the detected reflection in the image is taken into account when categorizing the reflection the invention allows for a much better evaluation whether a reflection is useful or not or even disruptive. For example, also reflections caused by spectacles worn by the user are not disruptive in principle if it is still possible to determine the property of the eye from the captured image. Therefore, it is necessary not only to determine which kind of reflection is detected in an image, like reflections from the eye or reflections from spectacles, but also the position of these reflections is essential for their categorization. This allows for a much more specific categorization of detected reflections, which in consequence allows for a much more distinctly control of the plurality of light sources. Advantageously, much more useful images, that are images which fulfil a predefined quality criterion, for example images out of which the property of the eye can be captured, can be obtained in a much shorter time without necessarily using plenty of light sources.

In an advantageous embodiment of the invention at least in dependence of the determined position, the at least one first reflection is assigned to a reflection category out of at least two different reflection categories, wherein if the detected at least one first reflection in the first image fulfils a predetermined definition of disruptive reflection the at least one first reflection is assigned to a first category of the reflection categories and if the at least one first reflection in the first image fulfils a predetermined definition of a useful reflection the at least one first reflection is assigned to a second category of the reflection categories. In that way detected reflections can easily be assigned to different reflection categories on the basis of their determined positions in the image. Furthermore, it is advantageous if an addition to the determined position also other criteria are used to categorize the reflections. So, different situations can be much better accounted for by this possibility of a very distinctive and individual categorization on the basis of the determined position.

Preferably, the position of the detected reflection is determined relative to a portion of a head of a user. Therefore, it is an advantageous embodiment of the invention that, if in the first image a portion of the head of the user is identified, a position of the portion is determined and the position of the detected at least one first reflection is determined relative to the position of the portion of the head. The portion of the head can be any portion, like for example, the nose or the mouth of a user or the ears or other significant and easy identifiable portions, like a head boundary and so on. But preferably, the position of the reflection is determined relative to an identified eye or eye portion of the user, if detected, because the relative position to the eye can be used as a crucial feature for deciding whether a reflection is disruptive or not. If a reflection for example is caused by spectacles of a user, the position of this reflection relative to the eye of the user decides whether this reflection actually is also disruptive for capturing the at least one property of the eye or not. Especially, this advantageous embodiment allows for the following categorization of detected reflections according to further embodiments of the invention.

Therein, the at least one first reflection fulfils the predetermined definition of a disruptive reflection if it fulfils at least one of the first criteria:

The detected at least one first reflection is determined not to be reflected by the user's eye;
The detected at least one first reflection is reflected by spectacles or glasses worn by the user;
The detected at least one first reflection has a size that is greater than a predetermined value.

Advantageously, these first criteria serve for at first finding potential candidates of disruptive reflections. But these first criteria can be seen as a necessary condition for being a disruptive reflection but not inevitably as a sufficient condition. Therefore it's a further advantageous embodiment of the invention that the at least one first reflection fulfils the predetermined definition of a disruptive reflection if it fulfils at least one of the second criteria:

The detected at least one first reflection occludes in the first image a portion of the eye, especially a portion that is required to determine the at least one property of the eye;
The detected at least one first reflection occludes in the first image a pupil of the eye partially or completely;
The detected at least one first reflection occludes in the first image an iris of the eye partially or completely;
The detected at least one first reflection occludes in the first image a sclera of the eye partially or completely;
The detected at least one first reflection occludes in the first image blood vessels of the eye partially or completely;
The detected at least one first reflection occludes in the first image an eye lid of the eye partially or completely;
The detected at least one first reflection occludes in the first image an eye lid corner of the eye partially or completely;
The detected at least one first reflection occludes in the first image a portion of the eye, where the detection of a useful reflection was expected.

So by these second criteria a reflection can more precisely be specified as being disruptive for capturing the at least one property of the eye of the user. Especially advantageous would be if a reflection has to fulfil at least one of the first criteria and at least one of the second criteria for being categorized as a disruptive reflection. The second criteria or at least one of them can then be seen as a sufficient condition for being a disruptive reflection. As mentioned, the first criteria serve for the purpose to at first find potential candidates for disruptive reflections, which are usually reflections that are not reflected by the user's eye, for example by spectacles or glasses or anything else. Those reflections can easily be identified e.g. by their size, as they are typically having a much greater size than reflections reflected by the user's eye, like glints or Purkinje images. But not each reflection that fulfils at least one of the first criteria automatically can be seen as a disruptive reflection. This is specified by the second criteria, by which it is made sure that the detected reflections, which are not reflected by the user's eye also actually complicate capturing the at least one property of the eye by occluding at least one part of the eye, which is necessary to detect for determining the property of the eye.

One of the second criteria is that the detected at least one first reflection occludes in the first image a portion of the eye, where the detection of a useful reflection was expected. This can be detected easily for example, if more than one light source illuminate the eye while capturing the first image it, because then it is expected that more than one reflection reflected by the eye, for example glints, can be detected. But if in this first image only reflections reflected by spectacles worn by the user can be detected and, furthermore, these reflections occlude some portions of the eye, it can be assumed that these reflections occlude these portions of the eye, where actually the glints should be detected. So, also in this case the detected reflections can be categorized as disruptive reflections.

Furthermore it is obvious that it is not necessary that a detected reflection fulfils all of the first and all of the second criteria to be categorized as disruptive reflection. Especially, which of the second criteria is suitable for identifying disruptive reflections strongly depends on which property of the eye shall be captured by the eye tracking device. If for example only the position of an eye of an user shell be determined, it is sufficient to detect at least part of the eye, like part of the pupil or part of the cornea and a reflection not reflected by the eye then is only disruptive if it occludes the complete eye so that a detection of the eye and its position is not possible. If on the other hand a gaze direction shell be determined by the eye tracking device on the basis of the detection of glints or other Purkinje images, it is necessary to detect at least one Purkinje image. So it is advantageous if these criteria are chosen by the use case itself. A further embodiment could also be that the fulfillment of an arbitrary subgroup of the first criteria and/or an arbitrary subgroup of the second criteria is a condition for assigning the at least one first reflection to the reflection category for disruptive reflections.

In a further embodiment of the invention during processing the first image the processing unit checks for at least one of the first criteria and/or at least one of the second criteria by analyzing the first image. The checking for the first criteria can for example be done by analyzing a detected reflection in the first image with regard to its size and/or its shape. Also the determined position of the reflection can be taken into account, for example for determining that the detected reflection is not reflected by the eye of the user, especially if it comprises a certain distance from the detected eye boundaries. For checking for the second criteria, first of all, parts of the eye of the user are determined by the processing unit, like the pupil, the iris, the sclera and so on, and the position of the detected reflection can be determined relative to these eye portions. If no eye portions can be determined by analyzing the first image, it also can be assumed that the detected reflection probably occludes the eye, or at least the eye portions that cannot be determined. Therefore, the detection of a disruptive reflection can be done in a very easy and effective manner. Similarly, the categorization of a useful reflection can be performed.

A very simple way to categorize a useful reflection is for example, that the detected at least one first reflection fulfils the predetermined definition of a useful reflection if it is not determined and/or categorized as disruptive reflection. In this way it is sufficient when the processing unit only checks for their first and second criteria and on the basis of the result of this checking the detected reflection can either be categorized as useful or disruptive. But also the definition of a useful reflection can be made more detailed to allow for a more detailed and situation adapted controlling of the light sources.

Therefore it is an advantageous embodiment of the invention when the detected at least one first reflection fulfils the definition of a useful reflection if it is not determined and/or categorized as disruptive reflection and fulfils at least one of the third criteria:

The detected at least one first reflection is a glint or a Purkinje image, especially a reflection from an outer surface of a cornea of the eye and/or from an inner surface of a cornea of the eye and/or from an anterior surface of a lens of the eye and/or from a posterior surface of a lens of the eye;

The detected at least one first reflection is reflected by a sclera of the eye;

The detected at least one first reflection is reflected by an eyelid of the eye;

The detected at least one first reflection is reflected by a face portion of the user different from the eye and eyelid, especially a face portion within a maximum distance from the eye;

The detected at least one first reflection is reflected by a front surface and/or a back surface of glasses of spectacles worn by the user.

Here also it is not necessary that all of the third criteria are fulfilled for categorizing a reflection as useful reflection. As already mentioned this strongly depends on the use case and which property of the eye should be determined by the eye tracking device. For determining a gaze direction Purkinje images play an important role. Especially, there are four Purkinje images, namely reflections from an outer surface of the cornea, from an inner surface of the cornea, from an anterior surface of the lens and from the posterior surface of the lens, wherein the first Purkinje image is also called glint. But also reflections from other parts of the eye, like reflections reflected by the sclera or by the eye lid and even by face portions can be used to determine for example the position of the face or head of a user relative to the camera and to determine or detect the position of the eye of the user in the image. Especially advantageous is the fact, that also reflections reflected by spectacles worn by the user can be not only categorized as non-disruptive but even as useful, which is explained later.

Preferably, during processing the first image the processing unit checks for at least one of the third criteria. On the basis of the result it can be easily decided whether a detected reflection is useful or not. Furthermore, this checking can again be done by analyzing a detected reflection in the image with regard to its size, its geometry and of course its position relative to the eye or eye portions.

On the basis of this detailed categorization of detected reflections, it is possible to achieve a very high eye tracking robustness by a corresponding controlling of the plurality of light sources in dependence of the categorization of a detected reflection, especially of each detected and categorized reflection separately, if more than one reflection is detected in the first image.

Therefore it is an advantageous embodiment of the invention that, when controlling the plurality of light sources in dependence of the categorization by changing the light intensity of at least one light source, the plurality of light sources is controlled such that the at least one first reflection is removed if it fulfils the predetermined definition of a disruptive reflection and/or at least one second reflection is produced in a second image that fulfils a predetermined definition of a useful reflection. Thereby, second images, especially subsequent to the first image, can be produced in a very effective way, which especially satisfy the predefined quality criterion, that can imply that these second images do not comprise any disruptive reflections anymore and useful reflections are produced in these second images with a sufficient quality to determine the at least one property of the eye.

Furthermore it is advantageous that, if the detected at least one first reflection neither fulfils the definition of a disruptive reflection nor the definition of a useful reflection it is categorized as neutral reflection and is assigned to a third reflection category. This additionally allows for an even more differentiated controlling of the light sources.

Furthermore, if the detected at least one first reflection is categorized as a disruptive reflection or a neutral reflection, at least one light source of the plurality of light sources can be determined as having emitted the light that causes the disruptive reflection or neutral reflection and a light intensity of the at least one determined light source is reduced, or especially the at least one determined light source is switched off, for capturing a second image. In general, reducing the intensity of a light source can also include the case that the light source is switches off completely. Thereby disruptive reflections can easily be removed, especially if the corresponding light source is switched off. It is also advantageous to switch off light sources which produce neutral reflections or at least to reduce their illumination intensity for power saving. Under some circumstances it may also be favourable not to switch off the light source producing a disruptive reflection but only to reduce its illumination intensity different from switching off, for example, if this light source is determined to produce a disruptive reflection and at the same time another useful reflection, so that by reducing the illumination intensity of this light source different from switching off the disruptive reflection on the first image appears as neutral reflection in a second image and the useful reflection caused by this light source can still be used for determining the at least one property of the at least one eye. This can similarly be applied to the controlling of light sources causing neutral reflections and useful reflection at the same time. In this case, the corresponding light sources are not switched off to remove the neutral reflections for power saving, as the useful reflections that are caused by these light sources are more important. To sum up, if a light source is determined to cause a disruptive reflection and/or a neutral reflection, the light source is switched off or at least its intensity is reduced, but only if the light source is not determined to cause a useful reflection at the same time.

Furthermore, if the detected at least one first reflection is categorized as a useful reflection and the predefined quality criterion is not satisfied, at least one quality feature is derived from the first image and at least one light source of the plurality of light sources is determined as having emitted the light that causes the useful reflection and a light intensity of the at least one determined light source is changed in dependency of the derived quality feature for capturing a second image. In other words, if a useful reflection is detected, the first image can be subjected to further image analysis to determine how the light source causing this useful reflection is controlled in its light intensity. Of course, it is not necessary to change the light configuration or the light intensity of the light sources if the quality of the first image and especially the quality of the identified useful reflections is good enough to capture the at least one property of the eye. But if not, the light sources can be controlled to optimize the image quality. To this end, the first image can be analyzed and it can be determined, for example whether detected useful reflections comprise enough saturation, whether their size is big enough or whether they are oversaturated. If more than one useful reflection is detected, also a distance of the useful reflections from each other can be determined, which is explained below. If the detected useful reflections are not saturated or bright enough or too small, the intensity of the corresponding light source can be increased. If the detected useful reflections are oversaturated, the illumination intensity of the respective light source is reduced. Thereby, the invention makes it possible not only to remove disruptive reflections but also to improve the image quality, and as a consequence also the tracking quality, significantly.

In an further embodiment, if at least two first reflections are detected that are determined to be reflected by the eye—and therefore they can be categorized as useful reflections—and the at least two first reflections are determined to comprise a distance from each other that is smaller than a predetermined value, the light sources that have emitted the light that causes the at least two reflections are determined and the intensity of at least one of the determined light sources is changed, especially switched off. Furthermore, a light source, having been inactive while capturing the first image, can be switched on for capturing a second image, if this light source is expected to produce a useful reflection. In other words, if two or more useful reflections are too close to each other the control unit can switch to a different light source configuration so that the resulting useful reflections in a further image a spaced further apart. Before switching to another configuration the eye tracking device can check, whether it can be expected that a new configuration will produce reflection spaced further apart, and only if this is so it is switched to the new light source configuration.

In a further advantageous embodiment of the invention at least one inactive light source of the plurality of light sources is determined to produce a useful reflection, especially a reflection reflected by the inner and/or outer surface of the cornea, and determined light source is switched on for capturing a second image. An inactive light source in this connection denotes a light source that was inactive and didn't emit light while capturing the first image. Thereby, the invention makes it also possible not only to determine light sources causing the reflections detected in the first image, but it is also possible to predict which of the light sources will cause useful reflections. This prediction can be done for example by analyzing the first image, especially on the basis of the position of the detected at least one first reflection. Furthermore, for determining this light source also a model of the eye and/or a model of a face of the user and/or a model of spectacles worn by the user and/or given positions of the light sources, especially relative to each other, and/or a given position of the imaging device, especially relative to each of the light sources, can be used and taken into account. Furthermore the position of the user and/or its face and/or its eyes relative to the capturing unit and the light sources can be determined on the basis of information from the first image and the above named models. In other words, a light source which is expected to produce useful reflections can be determined on the basis of geometrical considerations, especially on the basis of the geometrical correlation of the positions of the light sources relative to each other, relative to the imaging device, e.g. a camera, the disposition of the head of the user relative to the imaging device and light sources as well as the reflective behaviour based on the eye model. In the same way also the light sources that have produced a reflection in the first image can be determined.

Furthermore, the light source to be expected to produce a useful reflection can be determined on the basis of the position of the light source having been determined to emit the light, causing the detected at least one first reflection. So if in the first image, a reflection is detected and the light source causing this reflection is determined the position of this light source, the known relative positions to all the other light sources, can be used as additional information to determine light sources having been inactive while capturing the first image, which are expected to produce useful reflections. So lots of information can be derived from the captured image as well as from the known geometry of the eye tracking device that can be used to determine, which of the light sources having been active during capturing the first image, causes which reflection detected in the first image and which of the light sources inactive during capturing the first image are expected to produce useful reflections, so that on the basis of this analysis it can be predicted which lighting configuration is expected to produce the highest image quality and the control unit can control the light sources accordingly.

To further enhance this assignment of light sources to corresponding reflections and reflection positions it is a advantageous embodiment of the invention when each of the light sources has a specific characteristic different from each other, wherein the characteristic is provided by each of the light sources emitting light with a specific wavelength spectrum and/or the characteristic is provided by each of the light sources configured to emit light out of an emitting region having a distinctive shape each, wherein the distinctive shapes of the light sources differ from each other. Furthermore, the processing unit uses the specific characteristic to determine the light source having emitted the detected at least one first reflection. Thereby, the processing unit knows which light source has which emission characteristic. So advantageously, also specific emission characteristics can be used to identify light sources which produce a specific reflection.

Another possibility would be that in a step f) one light source of the plurality of light sources is switched on and a second image is captured, wherein the second image is compared to the first image and if a second reflection in the second image is determined on a second position that was not present in the first image, that one light source is determined of having emitted the light causing the second reflection. Thereby, it can easily be identified which light source causes which reflection.

Similarly another embodiment is that in a step g) one light source of the plurality of light sources, which has emitted light during capturing the at least one first image, is switched off for capturing a second image, the second image is captured and compared to the first image and if a reflection in the second image has disappeared compared to the first image, the one light source is determined of having emitted the light that caused in the first image the reflection that has disappeared in the second image. Also by this the light sources can easily be assigned to the reflections they caused.

In an further advantageous embodiment of the invention step f) and/or step g) can be repeated for a sequence of subsequent captured images, and in particular for each of the plurality of light sources, until it has been fully determined which light source produced which reflection and in particular on which position in the first image and the subsequent captured images so that also in further images it can be predicted which light source will produce which reflection and especially of which reflection category.

In other words by switching light sources on and off after each other it also can be identified which light source corresponds to which reflection as the corresponding reflections would appear or disappear correspondingly. This is a quite robust method for assigning light sources to their corresponding reflections but on the other hand the capturing of more images is necessary to implement this kind of assignment. Therefore, assigning light sources to their corresponding reflections they cause or are expected to cause by a prediction on the basis of the analysis of the first image as described above, especially before a different light source configuration is set for capturing a further image, is very advantageous and preferred. Also both methods for assigning can be combined, e.g. first the processing unit makes a prediction, and if this prediction does not lead to the end that the light source causing a specific reflection can be identified or no light source can be identified that is expected to produce a useful reflection, light sources can be switched on or off for their assignment to the corresponding reflections.

Therefore it is a further advantageous embodiment of the invention that the steps g) and/or f) are performed and especially repeated as described above, only if it cannot be univocally determined from the analysis of the first image and the position of a plurality of reflections in said first image which light source has produced which reflection.

Furthermore, if at least two reflections are detected as having been reflected by glasses worn by the user, a position of the glasses relative to the face of the user can be determined on the basis of the at least two detected reflections and their determined positions. In this case, reflections reflected by the glasses of a user are not categorized as being disruptive, in the contrast, they are even useful as can be used to determine the position of the glasses relative to the face of the user. This in turn provides information, which can be used to predict which of the inactive light sources can be expected to produce useful reflections and which of them not.

Moreover, there is another case in which a reflection by the glasses of a user can be very useful. Namely, if the detected at least one first reflection is determined to be reflected from glasses worn by a user—but not classified as disruptive reflection—a characteristic of the glasses, especially a refractive power of the glasses, is determined on the basis of the position of the at least one first reflection. Thereby, advantageously, the properties about the individuals eye wear can be determined. Especially it can be made use of detected reflections occurring at the front and the back of the lenses of the eye wear to evaluate and estimate the refractive power and curvature of the lenses. This information can further be used to enhance the tracking quality even more, especially by using the determined characteristic of the glasses to determine the at least one property of the user's eye. For example, this information about the refractive power and curvature of the glasses can be used to correct the gaze estimation. Thereby, reflections reflected by spectacles worn by the user can even contribute to enhancing the eye tracking quality. The same applies for contact lenses worn by the user.

Furthermore, it is advantageous if a light source of the plurality of light sources is determined to produce and/or to be expected to produce a disruptive or useful or neutral reflection by processing an input signal provided by accelerometer and/or magnetometer and/or attitude sensor that determines a spatial orientation of the eye tracking device with respect to the user's head and/or eye. Thereby the precision and the robustness of the operation of the eye tracking device can further be enhanced.

Furthermore, the capturing unit captures a second image while the at least one light source of the plurality of light sources emits light, the processing unit compares the first and the second image and if in the first image the at least one reflection was detected as a useful reflection and in the second image no reflection is detected in the determined position of the at least one reflection, a light source is determined that is expected to produce a useful reflection on the basis of the detected useful reflection in the first image and the determined light source is switched on for capturing a third image. For instance, it can happen that the path between a light source and the eye gets occluded by an object, for example the arm of the user. In the situation that the eye is still visible but one reflection is lost, which can be determined by comparing the first and the second image, in one or both of the eyes, the system can decide to switch to an alternative light source combination, for example the light source having caused the first reflection, that is lost in the second image, can be switched off and instead another light source can be determined that is expected to produce a useful reflection and this light source can be switched on. Thereby the tracking quality can be enhanced also in very difficult tracking situations. In general the second image can be any image being captured after the first image, but preferably the second image is an image captured subsequently after the first image without capturing an image in between. This applies similarly for the temporal relation of the third and the second image.

The eye tracking device according to the invention for capturing at least one property of at least one eye of a user comprises at least one imaging device capable of capturing images of the at least one eye of the user, a plurality of light sources capable of illuminating the at least one eye of the user, a processing unit capable of processing images captured by the imaging device and a control unit capable of controlling the plurality of light sources in their light intensity separately. Furthermore, the capturing unit is capable of capturing a first image while at least one of the light sources emits light. Moreover, the processing unit is capable of processing the first image and by processing the first image determining whether reflections are detected in the first image. If at least one first reflection is detected, the processing unit is further capable of determining a position in the first image of the at least one first reflection. Also the processing unit is capable of categorizing the first reflection at least on the basis of the position in the first image and capable of checking whether the first image fulfils a predefined quality criterion and if the first image does not fulfil the predefined quality criterion, the control unit is capable of controlling the plurality of light sources at least in dependence of the categorization by changing the light intensity of at least one light source of the plurality of light sources.

The preferred embodiments and advantages thereof described with regard to the method for operating an eye tracking device according to the invention correspondingly apply to the eye tracking device according to the invention. In particular, the described steps of the method for operating an eye tracking device and its embodiments according to the invention constitute further embodiments of the eye tracking device according to the invention.

In the following, advantageous embodiments of the present invention are described in more detail with reference to the accompanying drawings.

They show in.

This invention is based on a remote eye tracking device with at least one imaging device, like a camera, and a plurality of light sources. These light sources, when switched on, are reflected in the user's eye, face or glasses and are visible in the camera image as bright reflection spots. In general the term reflection in this application is used for a reflection defined as a connected region in an image comprising a level of brightness that is higher than the level of adjacent regions, especially higher than a predetermined value, and the boundary area between the reflection and adjacent regions comprises a gradient of brightness also greater than a predetermined value. These reflections, when they occur in the user's eyes (called glints) can be used to determine the location of the user's eyes and the gaze direction. Also reflections of the light source in several layers of the eye (Purkinje reflections) can help to determine the position and shape of the eye.

However, not all reflections are beneficial to the system, as they can confuse the system, overexpose the image or cover the glints or parts of the eye. In particular, a reflection covering the whole or part of the glints, pupil, iris, sclera, blood vessel, eyelid or eyelid corner is considered disruptive due to its negative impact on the robustness and accuracy of the gaze estimation. These disruptive reflections are often caused by glasses, which reflect the light from the light sources into the camera, as can be seen in FIG. 1.

Figure 1:
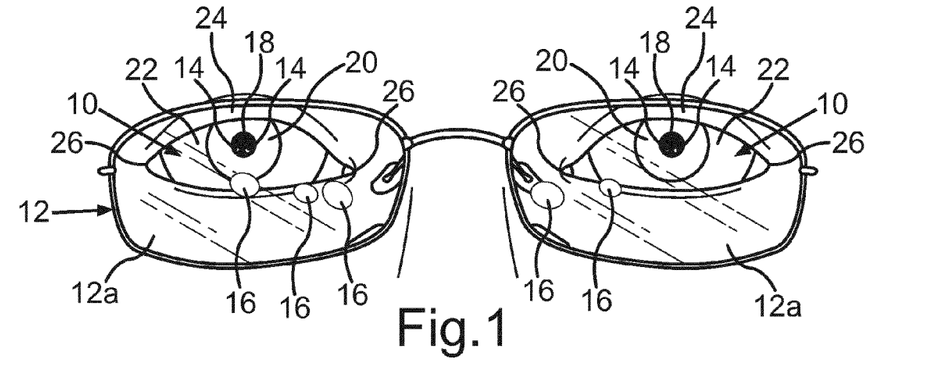
FIG. 1 a schematic view of an image of the eyes of a user wearing spectacles while a plurality of light sources illuminates the eyes of the user.

FIG. 1 shows a schematic illustration of an image of the eyes 10 of a user wearing spectacles 12 while a plurality of light sources of the eye tracking device illuminates the eyes. Thereby, the light sources causes reflections on the eyes, especially glints 14 as well as reflections 16 on the glasses 12a of the user's spectacles 12.

The suggested invention is a method to cope with these disruptive reflections. The system contains a control unit, which determines which of the reflections are beneficial, neutral or disruptive. In general, it switches off or reduces the intensity of light sources, which produce disruptive reflections, for example, by covering the glints 14 or interfering with some part of the eye like the pupil 18, iris 20, sclera 22, blood vessel, eyelid 24 or eyelid corner 26. Light sources which cause no useful reflections can optionally be switched off or the power can be reduced. Furthermore, the system switches on a light source or increases its intensity when it expects the light source to cause a useful reflection. But the controlling of the light sources in dependence of the reflection category can even be more detailed, as described in connection with FIG. 4 and FIG. 5.

Figure 2:
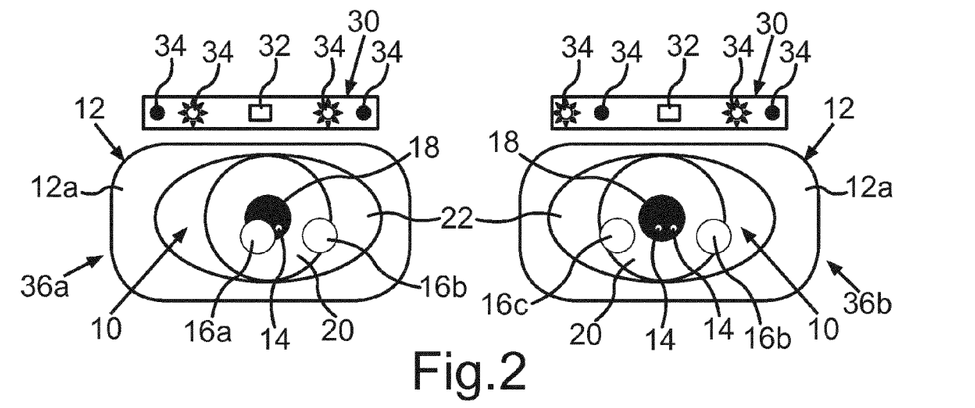
FIG. 2 a schematic illustration of the controlling of the light sources of an eye tracking device in the case that a disruptive reflection reflected from spectacles worn by the user occlude a useful reflection according to an embodiment of the present invention.

FIG. 2 illustrates how the eye tracking device 30 can be operated in the case a disruptive reflection 16a is detected. Users wearing glasses 12a cause tracking difficulties, as the light of the light sources 34 is reflected from the surface or the rim of the glasses 12a of the spectacles 12. These reflections can be dealt with as long as they do not cover the glints 14. When the reflections of the glass 12a cover or get close to the location of the reflections of the eye 10, according to this advantageous embodiment of the invention, a different set of light sources 34 can be used, thus removing the glass reflection or at least moving them away from the glints 14.

For this purpose, the eye tracking device 30 comprises an imaging device 32 and a plurality of light sources 34, in this example four light sources 34, as well as a processing unit for processing images 36a, 36b captured by the imaging device 32.

In general, the light sources 34 can be LEDs for example. Moreover, the light sources 34 can be capable of emitting infrared light, especially only infrared light and the imaging device 32, e.g. a camera, can be capable of capturing infrared light, especially only infrared light. Alternatively or additionally, the light sources 34 can be capable of emitting light in the visible wavelength region, especially some of the light sources 34 can be able to emit in the visible region and some of the light sources 34 in the infrared region or some of the light sources 34 can be able to emit in the visible region as well as in the infrared region, and the imaging device 32 can be able to detect light in the visible region. Moreover the eye tracking device 30 comprises a predefined capturing area, in particular the capturing area is defined as the region the imaging device 32 is capable of capturing images of. Furthermore the light sources 34 are arranged such that they are capable of illuminating the eye of a user in the capturing area of the eye tracking device 30.

Furthermore, the eye tracking device 30 comprises a control unit for controlling the light sources 34 separately in their intensity, especially for switching to different lighting configurations based on an analysis result of the captured image 36a, 36b. On the left hand side in FIG. 2 there is shown a schematic view of a captured image 36a, especially captured while two of the light sources 34 illuminating the eye 10. In this image 36a two reflections 16a, 16b can be detected that are reflected by the user's spectacles 12 as well as one reflection 14 which is reflected by the user's eye 10. In this case, one of the reflections 16a reflected by the user's spectacles 12 occludes an important portion of the eye 10, especially a portion where another glint 14 is expected. This left reflection 16a can be determined as disruptive reflection 16a by the eye tracking device 30, especially on the basis of the size of the reflection 16a, which identifies it as having been reflected from the spectacles 12, as well as on the basis of its position in the image 36a, especially relative to the eye 10 of the user. The eye tracking device than determines one of the light sources 34 having been active while capturing this first image 36a as having emitted the light causing the disruptive reflection 16a. After that this light source 34 is switched off thereby removing the disruptive reflection 16a and another of the light sources 34, which has not been active while capturing the first image 36a, is switched on, thereby producing another reflection 14, namely another glint 14, as can be seen from the second image 36b on the right hand side of FIG. 2. Thereby, the data quality can be increased.

A big advantage of this invention is that detected reflections are categorized on the basis of their position in the image 36a, 36b, especially their position relative to a detected eye 10 of the user. The positions, of the reflections as well as of the eye or eye portions, in the image can be determined e.g. as x- and y-coordinates each. Also the distance from the imaging device 32, i.e. the z-coordinate, can be derived from the image 36a, 36b, e.g. from the dimensions in the image of eye features which do not change dynamically, such as limbus major and minor axis, or eye ball radius.

Thereby, images 36a, 36b can be captured and used for determining the at least one property of the eye 10 even if in the images 36a, 36b reflections 16b, 16c reflected by the spectacles 12 of a user are present.

Therefore, the important criteria for categorizing a reflection as disruptive reflection is not only that the reflection is not reflected by the user's eye 10 but also that this reflection occludes an important part of the user's eye 10. Furthermore, the reflection reflected by the user's spectacles 12 can even be used for increasing the eye tracking quality further. The reflections of the light sources 34 reflected by the user's spectacles 12 provide information about properties of the glasses 12a worn by a user. They allow an estimation of the curvature and refractive properties in each area of the glass 12a, which can then be used to correct the determined eye 10 position and gaze direction using this information. So additionally, for individual glasses 12a or spectacles 12 the eye tracking device 30 uses the non disruptive reflections on the glasses 12a to determine some properties about the individual's eye wear. It makes use of the reflections occurring at the front and the back of the lenses to evaluate and estimate their refractive power and curvature to use this information for correcting the gaze estimation, which is explained in more detail below with reference to FIG. 6 and FIG. 7.

Figure 3:
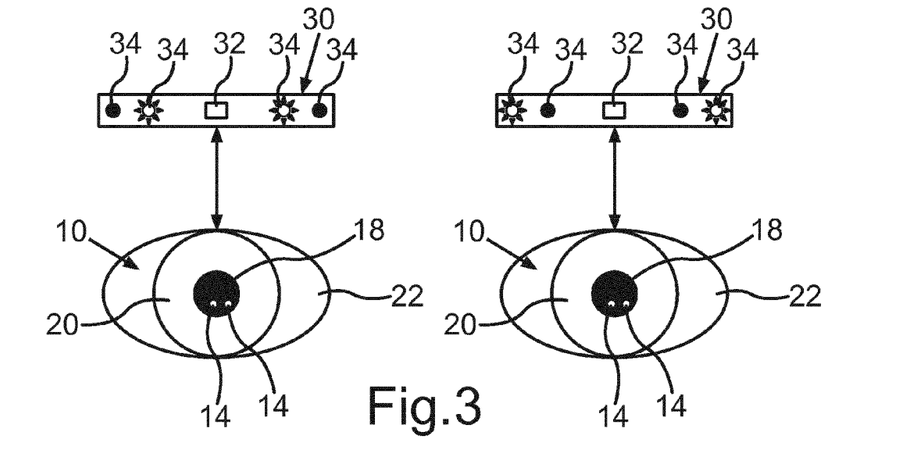
FIG. 3 a schematic illustration of controlling the light sources of an eye tracking device in the case that detected useful reflections are too close to each other according to a further embodiment of the present invention.

FIG. 3 shows a schematic illustration for operating the eye tracking device 30 according to another embodiment of the invention. The eye tracking device comprises the same components as already explained with regard to FIG. 2. Now a first image 36a is captured by the imaging device 32, which shows the eye 10 of a user, in this case without spectacles 12. When the distance between the eye tracking device 30 and the user increases, the distance between the reflections of the different glints 14s in the image of the user's eye 10 decrease. At some point the reflections 14 move together so closely that it is difficult or even impossible to distinguish the individual reflections 14, which is illustrated by the first image 36a on the left hand side of FIG. 3. The eye tracking device 30 is able to detect this and switch to a different combination of light sources 34, thus increasing the distance of the reflections 14 visible in the camera 32. This can be seen in the second image 36b on the right hand side of FIG. 3. So by controlling the light sources 34 in dependence of the positions of the detected useful reflections 14 as described the tracking range can advantageously be extended.

Furthermore, the invention makes it possible to cope with further difficult situations. For example, the invention also enhances eye tracking under extreme angles of rotation. In some situations, the user might not be facing the camera 32 but the head can be rotated away significantly. In this situation the eye tracking device 30 will be able to benefit from using the light sources 34 on the one side of the camera 32 rather than using one light source 34 on either side. This effect occurs due to the reduced risk of occlusion, e.g. from the nose, and the decreased acuteness of the angle between the light source 34, the eye 10 and the camera 32. In this case, the imaging device 32 can capture a first image and by analyzing this image by the processing unit detected reflections can be categorized on the basis of their positions in the image. If the image does not fulfil a predetermined quality criterion, which can be the case when the head is rotated away significantly, light sources 34 can be determined which are expected to produce useful reflections. To determine these light sources 34 lots of information can be taken into account, for example, the positions of the detected reflections, the positions of the light sources 34 having caused these reflections, the position of the head relative to the light sources 34 and the camera, the camera position itself, an eye 10 model or a face model, and so on. By this, the system can automatically choose a lighting configuration which enhances the eye tracking quality.

Furthermore, the reconstruction accuracy can also be increased. The contours of a reflection in the eye 10 can only be obtained up to a certain amount of accuracy due to the small size of the reflection. With additional light sources 34, it will be possible to obtain more reflections in each eye 10. This provides the eye tracking device 30 that detects the glints 14 with additional information potentially increasing the reconstruction accuracy. This is also made possible by the detection of reflections and their positions, by the categorization of these reflections on the basis of their positions, as well as by determining light sources 34 causing the respective reflections as well as by determining light sources 34 which are expected to produce useful reflections. Thereby, the number of light sources 34 illuminating the eye 10 without causing disruptive reflections can be maximized.

Furthermore, when using a remote eye tracking device it can happen that a path between the light sources 34 and the eye 10 gets occluded by an object, for example the arm of the user. In the situation that the eye 10 is still visible but one reflection is lost in one or both of the eyes 10, the eye tracking device 30 can decide to switch to an alternative light source combination. This can be achieved for example by comparing successive images captured by the imaging device 32. If in a first image a useful reflection on a certain position is detected but in a successive image this useful reflection on the certain position is not detected anymore, the eye tracking device can determine the light source having caused the useful reflection in the first image, switch it off and instead switch another light source 34 on which is expected to produce an other useful reflection.

So by actively and dynamically controlling which light sources 34 are switched on or off or varied in their light intensity at a certain time in order to prevent disruptive reflections and produce useful reflections the tracking quality and tracking robustness can be increased in many different and also difficult tracking situations.

Figure 4:
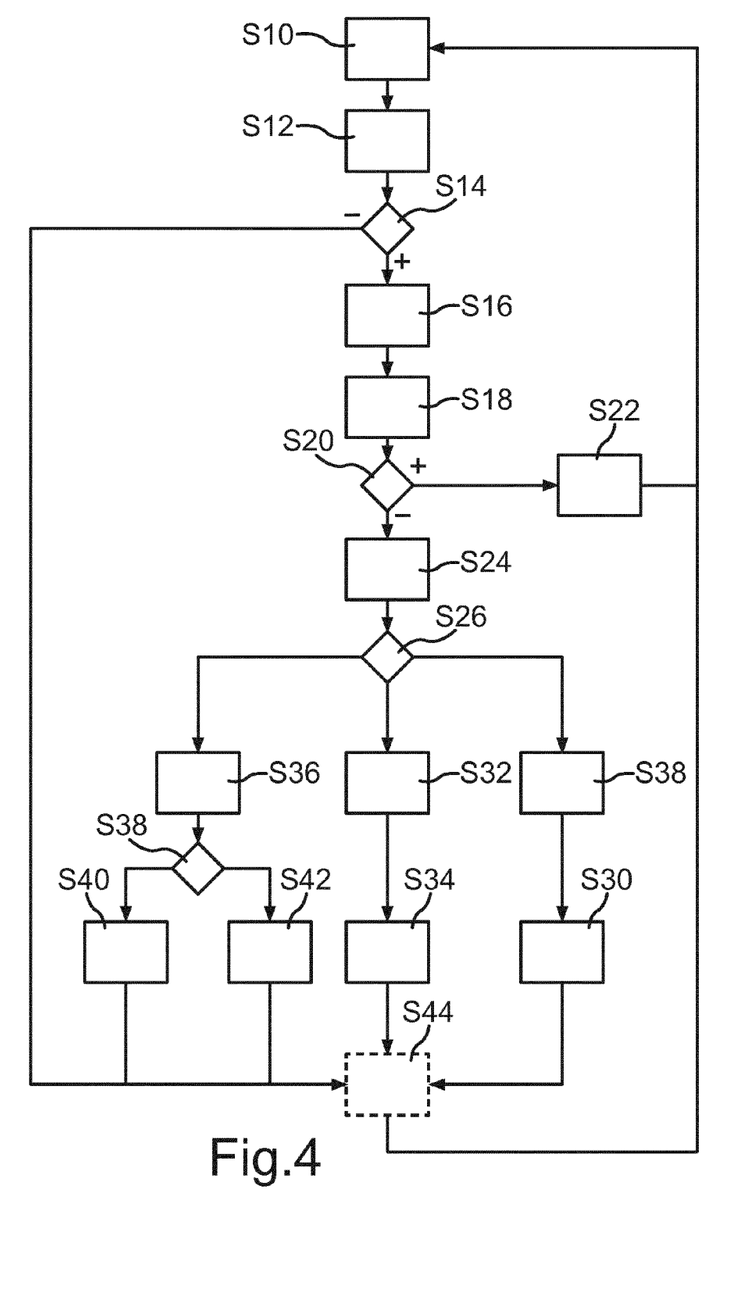
FIG. 4 a schematic illustration of a method for operating an eye tracking device according to a further embodiment of the invention.

FIG. 4 shows a schematic illustration of a method for operating an eye tracking device 30 according to an embodiment of the present invention. This method starts in step S10 when a first image of a user in a capturing area of the eye tracking device 30 is captured by the imaging device. In the next step S12 the processing unit processes the first image and by processing the first image the processing unit determines whether reflections are detected in the first image. If in step S14 the condition, that at least one first reflection is detected in the first image, is satisfied, the method proceeds to step S16, where the position in the first image of the at least one reflection is determined. Thereby, also the position of the eye 10 of the user, if detected, or at least a part of the eye 10 of the user is determined and the position of the at least one reflection is determined relative to the position of the eye 10 of the user. After that, in step S18 the first reflection is categorized at least on the basis of the position in the first image. Additionally it can be categorized also on the basis of its size or shape to be able to distinguish between reflections reflected by the eye 10 of the user and reflections not reflected by the eye 10 of the user. Preferably, there are at least three different reflection categories, one for disruptive reflections, one for useful reflections and one for neutral reflections. A detected reflection can for example be assigned to the reflection category for disruptive reflections if it is determined that a detected reflection is not reflected by the user's eye 10, or especially is reflected by spectacles 12 worn by the user, which can for example be determined by the size of the detected reflection, and additionally if it is determined that this reflection at the same time occludes a significant portion of the eye 10 which is required to determine the at least one property of the eye 10, for example a significant portion of the pupil 18, the iris 20, the sclera 22, the blood vessels, or also of the eyelid 24 or eyelid corners 26. Furthermore, a reflection is preferably assigned to the reflection category for useful reflections if the reflection is a glint 14 or a Purkinje image or is reflected by the sclera 22. It can also be seen as a useful reflection if it is reflected by an eyelid 24 of the eye 10, by a face portion of the user, especially in the eye 10 region, or even if the detected reflection is not categorized as disruptive reflection and is reflected by glasses 12a of spectacles 12 worn by the user, which can be used to determine some properties of the individual's eyewear. All other reflections can be categorized as neutral reflections.

So if now in step S18 the determined reflection is categorized in step S20 the eye tracking device 30 checks whether the first image fulfils a predefined quality criterion. This quality criterion may consist in that in the first image at least one useful reflection is detected and the at least one property of the eye 10 can be determined on the basis of this useful reflection. This quality criterion can further additionally consist in that the detected useful reflection has to comprise a certain predefined saturation or brightness or size. Furthermore, the quality criterion can also consist in that different eye 10 portions, like the pupil 18, the iris 20 and the sclera 22, have to comprise a certain contrast between each other that is required for determining the individual eye 10 portions with a certain minimum accuracy. So if in step S20 it is determined that the predefined quality criterion is satisfied, the at least one property of the eye 10 can be determined in step S22 and the method starts again from step S10 by capturing another image.

But if in step S20 it is determined that the quality criterion is not satisfied, the method moves to step S24 for controlling the plurality of light sources 34 at least in dependence of the categorization by changing the light intensity of at least one light source 34 of the plurality of light sources 34. To this purpose first of all it is checked to which reflection category the detected reflection has been assigned to in step S26. If a reflection was determined as being a disruptive reflection, the method moves to step S28, where it is determined which of the light sources 34 having been active when capturing the first image has emitted the light causing the disruptive reflection. After that, the determined light source 34 is turned off in step S30, or at least its illumination intensity is reduced. If in step S26 it is determined that the detected reflection was categorized as neutral reflection the method moves to step S32, where the eye tracking device 30 determines which of the light sources 34 having been active during capturing the first image has emitted the light causing the neutral reflection and after that in step S34 the determined light source 34 is also switched off or at least its intensity is reduced for saving power.

Here it has to be pointed out that there is still a difference in controlling the light sources in the cases of disruptive and neutral reflection. The removal of the disruptive reflection has a very high priority in comparison to the removal of a neutral reflection, but there have to be other aspect to be taken into account. E.g. if a light source produces a useful reflection and at the same time a neutral reflection, this light source is not switched off at any circumstances for capturing a further image, because then the useful reflection would be lost also. But if a light source produces a useful reflection and at the same time a disruptive reflection, so that the at least one property of the eye can't be determined because of this disruptive reflection, the disruptive reflection has to be removed. So at least the light intensity of the light source hat to be reduced, and if this doesn't help, the light source has to be turned off.

Furthermore, if in step S26 it is determined that the detected reflection was categorized as useful reflection the method moves to step S36 where the first image is analyzed further by the processing unit. This analysis is done for the purpose of finding out how the quality of the useful reflection can be improved. For this purpose, saturation, brightness or size of the useful reflection can be determined. If it is decided in step S38 that the useful reflection is not saturated enough, not bright enough or too small, the method moves to step S40 where the control unit compose the light sources 34 in that way, that the light source 34 having emitted the light having caused the useful reflection is increased in its intensity. If on the other hand in step S38 it is decided that the detected useful reflection is oversaturated, to bright or too big the method moves to step S42 where the intensity of the light source 34, which is determined of having emitted the light causing the useful reflection is reduced. Moreover, if in step S38 it is decided, that there are more then one useful reflection and the useful reflection are too close to each other, the control unit can switch to a different light configuration, e.g. turn one light source having caused one of the useful reflections off and switch another one on which is expected to produce a useful reflection (S44).

So after the steps S30, S34, S40 and S42 the method can move again to step S10, where another image is captured by the imaging device. But before doing so, there can be an optional additional step S44. In this step S44 the eye tracking device 30 determines on the basis of the image information of the first image and optionally on the basis of additional information which of the plurality of light sources 34, which has not been active while capturing the first image, is expected to produce a useful reflection and after this determination this light source 34 or these light sources 34 are switched on.

Figure 5:
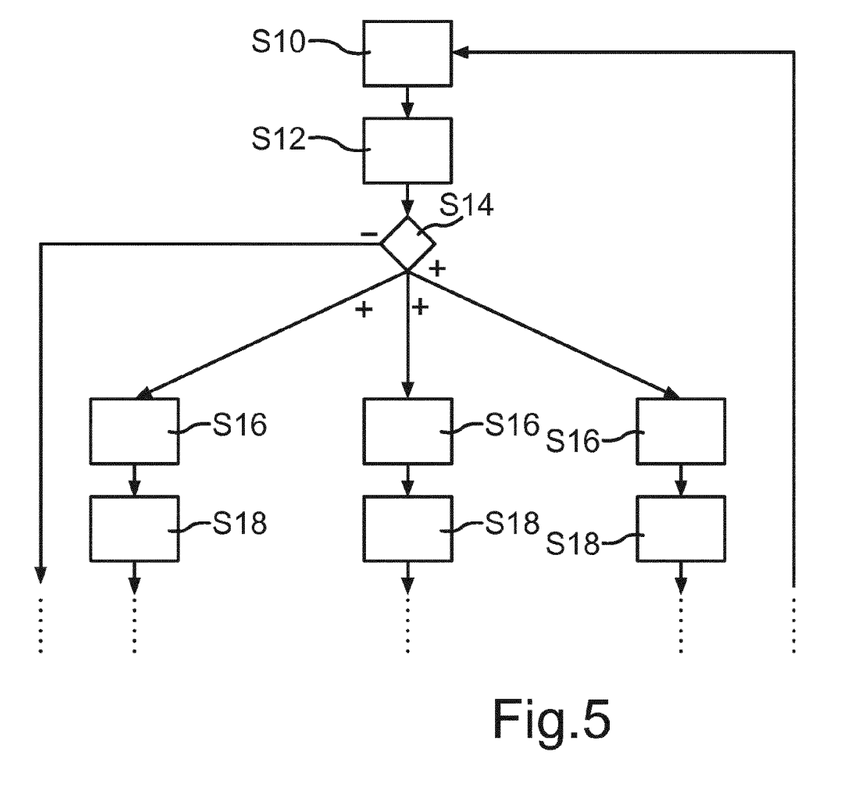
FIG. 5 a schematic illustration of a method for operating an eye tracking device according to another embodiment of the present invention.

This procedure can also be performed if in the first image several different reflections are detected, which should be illustrated by FIG. 5. Here the method starts again in step S10 when a first image is captured by the capturing device and this image is processed in step S12 by the processing unit. If now in step S14 it is determined that several reflections, in this example three reflections, are detected the method proceeds to a step S16 for each of the detected reflections. So for a first reflection a corresponding position in the image is determined and a reflection is categorized in step S18 and so on. For the second reflection its position in the image is determined and the reflection is categorized in step S18 and so on. And also for the third reflection its position is determined and in step S18 the reflection is categorized and so on. The method now proceeds analogous to the method described with respect to FIG. 4 for each of the detected reflections.

Figure 6:
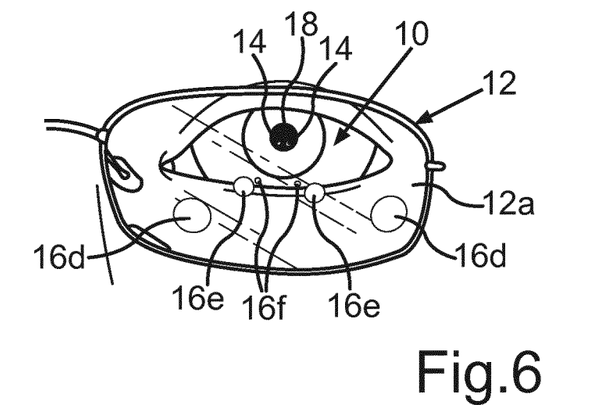
FIG. 6 a schematic illustration of an image of the eyes of a user wearing spectacles to illustrate different kinds of reflections reflected by the glasses of the spectacles.
Figure 7:
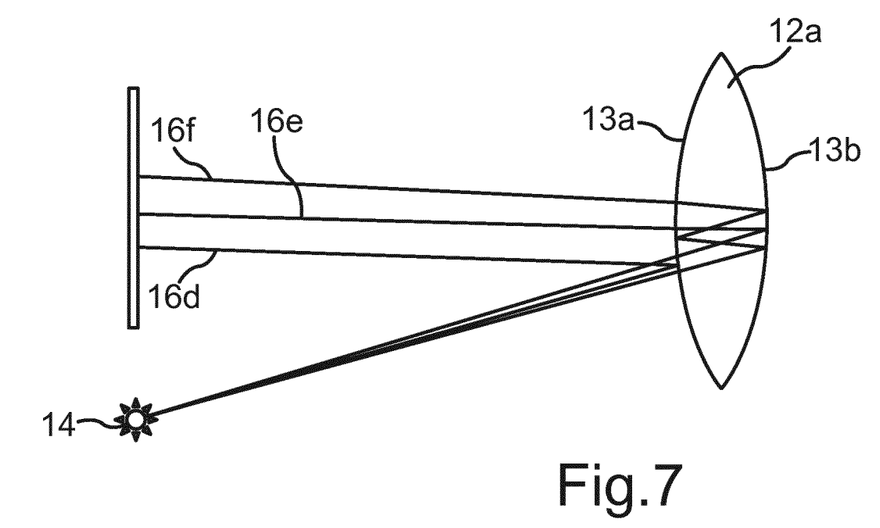
FIG. 7 a schematic illustration of the reflection of light of a light source of the eye tracking device at a spectacles glass of a user, the light being reflected in three different ways by the spectacles glass.

Now with reference to FIG. 6 and FIG. 7 it is explained, how non disruptive reflections 16d, 16e, 16f on the glasses 12a of a user can be used to determine some properties about the individual's eye wear.

According to an embodiment of the invention, the refractive power of the glasses a user is wearing is calculated. The most common tool to perform this measurement is to use a lensmeter, which is an instrument to measure the refractive power of lenses, for example glasses and contact lenses. It can measure the spherical refractive power, the cylinder, the axis as well as some other information about glasses, for example if they are varifocal or not.

Some lensmeters require a human to take the measurements and look at the results; others do all the measurements automatically after the lens has been placed in the correct position. Both manual as well as automatic lensmeters work by trying to find the settings that neutralize the power of the lens being measured.

For the manual version, the optician will change the settings of the lensmeter until s/he can see a set of pronounced and straight lines. The settings when this state is reached show the dioptres of the lens in question. For the cylinder angle and strength a different set of knobs is used.

For an automatic lensmeter the measurements of the lens are obtained by finding the front and back vertex power and the distortion of the light pattern. The distortion is used for calculating the cylinder.

A detailed description of lensmeters (also called focimeter) can be found in D. Kerr's description "The Focimeter—Measuring Eyeglass Lenses" (Dec. 7, 2010). Furthermore, focimeters are defined under the iso standard "ISO 8598-1: 2014".

According to an embodiment of the invention the eye tracking device 30 is used to evaluate the refractive power of the glasses 12a worn by a user. One important characteristic of glasses 12a is that their main refractive power comes from the back side, i.e. the side which is closer to the eye 10. For an eye tracking device 30 that means that it will somehow be necessary to not only look at the reflection of the outside surface of the glass 12a, but also get a reflection from the inner surface.

FIG. 6 shows a schematic illustration of an image of an eye 10 of a user wearing spectacles 12. In this image, multiple reflections 14, 16d, 16e, 16f are visible. The large reflections 16d are the reflections from the outer surface, the medium reflections 16e are reflections from the inner surface and finally the small reflections 16f are the second reflection from bouncing back and forth between the inner and outer surface. The two reflections 14 directly at the pupil 18 come from the cornea.

For further illustration FIG. 7 shows a schematic illustration of the light of a light source 34 of the eye tracking device 10 being reflected in these three different ways by a glass 12a of spectacles of a user. The light reflected by the outer surface 13a of the glass 12a causes large reflections 16d in the image, the light reflected by the inner surface 13b of the glass 12a causes the medium reflections 16e and the light repeatedly reflected by the outer surface 13a and inner surface 13b of the glass 12a causes the small reflections 16f.

These reflections 16d, 16e, 16f can be used to estimate the curvature of the glasses 12a. Additional reflections through the use of extra light sources 34, in particular LEDs, will help to increase the accuracy of the estimation of the refractive power, especially when the LEDs are not collinear.

In general, every reflection 16d, 16e, 16f we can see in the glasses 12a gives us two pieces of information: the X and the Y component of the center of the reflection 16d, 16e, 16f, i.e. the x-coordinate and the y-coordinate of the position of the reflection 16d, 16e, 16f in the image.

To be able to calculate the refractive power of the glasses 12a we need to make some assumptions on what kind of models can be used for the glasses 12a. Here a choice has to be made between simple models, which only model the most basic glasses 12a accurately and model other glasses 12a inaccurately. However, such a simple model is very easy to learn quickly with little information. Here a short description of the models that can be used. Each of these glass models has a number of constant unknowns, because the glasses 12a themselves do not change in the process.

Every model has 5 unknowns that change in every frame, i.e. every captured image, which are the position and the orientation of the lens, i.e. the glass 12a. These 5 unknowns have to be obtained in every frame before any additional information can be learned about the glass characteristics.

According to a thin lens model the number of constant unknowns is 1 (spherical). The thin lens model is a common description of lenses whose thickness is negligible compared to the radii of curvature of the lens surfaces. Its refractive power is solely described by the focal length of the lens.

According to a basic model the number of constant unknowns is 1 (spherical). The basic model (or thick spherical lens) assumes that the two surfaces on both sides of the lens are perfect spherical. Like the thin lens model, this model is described by one parameter, the focal length, which can easily be learned due to the low amount of information required in every frame. Together with the 5 changeable unknowns and the 1 constant unknown it is only necessary to find the center of three reflections 16d, 16e, 16f on the glasses 12a to learn something about the glasses 12a.

According to a astigmatic model the number of constant unknowns is 3 (spherical, cylinder axis and cylinder strength). This model is required for glasses 12a for people with astigmatism. These do not only have a spherical component that is consistent in all directions, but it has a different effect in one direction. Due to the 3 unknowns it is already necessary to see four reflections 16d, 16e, 16f to reconstruct the whole lens from one frame only. However, even having only three reflections 16d, 16e, 16f in several different frames is enough to learn the parameters of the glass 12a more and more accurate over time, which is explained below.

According to a varifocal model the number of constant unknowns is 4 (spherical, cylinder axis, cylinder strength and near component). Varifocal lenses are like astigmatic ones but they have a second section on the lens with a different refractive power. This is usually used to be able to see in the far distance, but also be able to read a book.

On the basis of these models the glasses 12a worn by a user can be learned by the eye tracking device 30, especially in the following ways:

As mentioned above, each reflection 16d, 16e, 16f that we can find on the glasses 12a, identify as a reflection and match to one of the LED provides us with two pieces of information. The X and the Y component of the reflection 16d, 16e, 16f can be used to calculate all the unknowns, the variable and the constant ones.

An additional set of information is that the left and the right glass 12a always have the same orientation and position relative to each other. Thus when the orientation and the position of one glass 12a is known, we can also calculate the position and orientation of the other, once we have obtained their relative positions once. The same is true, if we know the orientation of one glass 12a and the position of the other. In that situation we can obtain the missing information without requiring extra information.

Furthermore, we can learn the relative position between the glasses 12a and the eyes 10. Once we learnt this relative position and orientation, it will be possible to use this information to be able to learn more with fewer reflections 16d, 16e, 16f. However, care needs to be taken with this point, as the relative position between eyes 10 and glasses 12a can change when the user moves the glasses 12a consciously or subconsciously.

With all this information we can apply some sort of learning method to get from the reflections 16d, 16e, 16f and the relative positions and orientations to a learned glass model. The list of learning methods that could be used is large; however, there is one requirement for the method of choice, namely it has to be robust to outliers and noise, as detecting the center of the large reflections 16d, 16e, 16f accurately and always correctly identifying the type of reflection 16d, 16e, 16f and the LED that is causing it is difficult.

One can think about many different learning techniques which all have the one thing in common: Using the information about the observed centers of reflections 16d, 16e, 16f in the frames to somehow fit a lens model to the seen data and learn the lens parameters over time.

Learning Method I: Two-Staged:

One possibility of a learning technique has two stages: The first stage calculates in a single frame estimated glass strength. Afterwards, all these values have to be combined over time to get a stable and correct refractive power for a lens.

Obtaining Glass Strength for a Single Frame:

One option is to use a supervised learning method by gathering data before hand and then using this data to gain an understanding what kind of reflection arrangements are caused by glasses 12a of different strength.

In this case, the obtained test data have to be annotated automatically or manually. For the glasses method many participants with glasses 12a with known strength could be used and the glass strength entered into a database. Then we could automatically try to find all the reflections 16d, 16e, 16f and learn a model or function that links reflection position to glass strength; potentially with the help of other values like calculated eye position, size of glasses 12a, etc.

Alternatively, we can use the models above to calculate the glass strength in every frame from all the information we have available.

Calculating Glass Strength Over Time:

The problem with the above is that for each single frame the glass strength is going to be quite inaccurate. This has multiple reasons:

Calculating the center of the reflection 16d, 16e, 16f or to be more exact the brightest point of the reflection 16d, 16e, 16f (many pixels are saturated, so difficult to figure out) is always prone to an error. The reflections 16d, 16e, 16f can be distorted due to the shape of the glass 12a, can be cut off due to the frame of the glasses 12a or can merge.

The type of reflection 16d, 16e, 16f will be difficult to understand in many situations, as well as the LED that is causing the reflection 16d, 16e, 16f.

Many frames are not going to have enough reflections 16d, 16e, 16f and other information to learn a lot from them.

So here we need a method that can robustly adjust the model over time without being impacted majorly in case of incorrect or limited amounts of data. Some methods are including but not limited to RANSAC, particle filtering and Expectation Maximization.

RANSAC: All the glass strengths that have been obtained over a set of frames can be run through RANSAC to find the one most likely to be the correct one. RANSAC is very good at avoiding outliers, but is computationally quite expensive and is not proven to converge to the optimal solution although experiments show that it does. RANSAC can also be combined with any optimization methodology.

Particle Filtering: Particle Filtering works by creating a set of potential glass strengths and modifying these randomly on every frame. When a new set of observations comes in, for example through a frame in which reflections can be seen, each particle is given a probability on how likely it is to match the current observations. These probabilities are then used to create a new set of particles. Afterwards, a clustering method could be used to find the best glass strength from the particles. The disadvantage of this method is that the currently best glass strength can jump around in the case when there are multiple clusters.

Expectation Maximization: We can represent each of the unknowns of the glass strength as a statistical distribution. In Expectation Maximization we want to use the observations that we make in terms of reflections to find the best explanation in terms of glass properties for the reflections 16d, 16e, 16f. The one with the highest probability is the one that we can use for an estimate of the glass strength.

With these learning methods we will be able to calculate the refractive power of the glasses 12a and use these values to improve eye tracking quality.

Learning Method II: Best Fit:

This method is learning the glass parameters by doing a best fit of the lens to the observed reflections in the image. At each time, the algorithm has a hypothesis of the parameters of the lens model. At the start, these parameters may be entered manually or they may be set to default values.

In each frame, the position and orientation of the glass 12a is obtained by doing a best fit (the 5 unknowns are position and orientation, the given data is the observation of the reflections in the frame). A best fit algorithm finds the values for the unknowns (position/orientation of lens in the space) such that it fits the observed reflections 16d, 16e, 16f as best as possible. As error functional, one can e.g. compute for a given lens position/orientation the theoretical position of reflections 16d, 16e, 16f in the image and compare it with the observed reflection position (e.g. use squared distance norm or any other metric to measure fitness of the model). This error functional can be minimized by any local and global minimization method, e.g. steepest gradient method, Nelder-Mead, genetic algorithms, direct or randomized sampling, or others.

If this fitting problem is overdetermined (i.e. if at least 3 reflections 16d, 16e, 16f are observed which give 6 conditions for the 5 unknowns position/orientation), then the result of the best fit will not be perfect, i.e. the error functional will not be 0. This information can be used to learn about the internal model parameters, e.g. the focal length of a thin lens model or the parameters of another lens model.

Now, that the position/orientation is known all other parameters can be adapted to even lower the value of the error functional. This adaption can be done in several ways as already described. Adaptations on the model parameters should always be robust and smooth over time. One could directly minimize the error functional for the model parameters as unknowns and smooth these results over time. Outliers should be discarded. Alternatively, one can just slowly converge the model parameters into negative gradient direction of the error functional.

However the model parameters are adapted, if the adaption lowers the error functional and if this algorithm is used for reconstructing lenses whose parameters do not change over time, then the computed model parameters will converge against the real parameters.

To conclude this invention describes an eye tracking device and a method for operating an eye tracking device, which improve the tracking robustness by actively controlling a set of light sources in dependence of determined reflection categories based on the positions of the detected reflections and thereby eye tracking can be performed also in very difficult situations with high quality.

The invention claimed is:

1. Method for operating an eye tracking device (30) for capturing at least one property of at least one eye (10) of a user, wherein the eye tracking device (30) comprises at least one imaging device (32) capable of capturing images (36a, 36b) of the at least one eye (10) of the user, a plurality of light sources (34) capable of illuminating the at least one eye (10) of the user, a processing unit capable of processing images (36a, 36b) captured by the imaging device (32) and a control unit capable of controlling the plurality of light sources (34) in their light intensity separately, the method comprises the steps:

a) the imaging device (32) captures a first image (36a) while at least one of the light sources (34) emits light; and
   b) the processing unit processes the first image (36a) and by processing the first image the processing unit determines whether reflections (14; 16; 16a; 16b; 16c; 16d; 16e; 16f) are detected in the first image;

characterized by the following steps:
   c) if at least one first reflection (14; 16; 16a; 16b; 16c; 16d; 16e; 16f) is detected, a position in the first image (36a) of the at least one first reflection (14; 16; 16a; 16b; 16c; 16d; 16e; 16f) is determined;
   d) the first reflection (14; 16; 16a; 16b; 16c; 16d; 16e; 16f) is categorized at least on the basis of the position in the first image (36a); and
   e) if the first image (36a) does not fulfil a predefined quality criterion, controlling the plurality of light sources (34) at least in dependence of the categorization by changing the light intensity of at least one light source (34) of the plurality of light sources (34).

2. The method according to claim 1,
   characterized in that
   at least in dependence of the determined position the at least one first reflection (14; 16; 16a; 16b; 16c; 16d; 16e; 16f) is assigned to a reflection category out of at least two different reflection categories, wherein if the detected at least one first reflection (14; 16; 16a; 16b; 16c; 16d; 16e; 16f) in the first image fulfils a predetermined definition of a disruptive reflection the at least one first reflection (14; 16; 16a; 16b; 16c; 16d; 16e; 16f) is assigned to a first category of the reflection categories and if the at least one first reflection (14; 16; 16a; 16b; 16c; 16d; 16e; 16f) in the first image fulfils a predetermined definition of a useful reflection the at least one first reflection (14; 16; 16a; 16b; 16c; 16d; 16e; 16f) is assigned to a second category of the reflection categories.

3. The method according to claim 1,
   characterized in that
   if in the first image (36a) a portion (10; 18; 20; 22; 24; 26) of the head of the user is identified, a position of the portion (10; 18; 20; 22; 24; 26) is determined and the position of the detected at least one first reflection (14;

16; 16a; 16b; 16c; 16d; 16e; 16f) is determined relative to the position of the portion (10; 18; 20; 22; 24; 26) of the head.

4. The method according to claim 1, characterized in that
the at least one first reflection (14; 16; 16a; 16b; 16c; 16d; 16e; 16f) fulfils the predetermined definition of a disruptive reflection if it fulfils at least one of the first criteria:
the detected at least one first reflection (14; 16; 16a; 16b; 16c; 16d; 16e; 16f) is determined not to be reflected by the user's eye (10);
the detected at least one first reflection (14; 16; 16a; 16b; 16c; 16d; 16e; 16f) is reflected by spectacles (12) or glasses (12a) worn by the user;
the detected at least one first reflection (14; 16; 16a; 16b; 16c; 16d; 16e; 16f) has a size that is grater than a predetermined value.

5. The method according to claim 4, characterized in that
during processing the first image (36a) the processing unit checks for at least one of the first criteria and/or at least one of the second criteria by analyzing the first image (36a).

6. The method according to claim 1, characterized in that
the at least one first reflection (14; 16; 16a; 16b; 16c; 16d; 16e; 16f) fulfils the predetermined definition of a disruptive reflection if it fulfils at least one of the second criteria:
the detected at least one first reflection (14; 16; 16a; 16b; 16c; 16d; 16e; 16f) occludes in the first image (36a) a portion of the eye (10), especially a part that is required to determine the at least one property of the eye (10);
the detected at least one first reflection (14; 16; 16a; 16b; 16c; 16d; 16e; 16f) occludes in the first image (36a) a pupil (18) of the eye (10) partially or completely;
the detected at least one first reflection (14; 16; 16a; 16b; 16c; 16d; 16e; 16f) occludes in the first image (36a) an iris (20) of the eye (10) partially or completely;
the detected at least one first reflection (14; 16; 16a; 16b; 16c; 16d; 16e; 16f) occludes in the first image (36a) a sclera (22) of the eye (10) partially or completely;
the detected at least one first reflection (14; 16; 16a; 16b; 16c; 16d; 16e; 16f) occludes in the first image (36a) blood vessels of the eye (10) partially or completely;
the detected at least one first reflection (14; 16; 16a; 16b; 16c; 16d; 16e; 16f) occludes in the first image (36a) an eye lid (24) of the eye (10) partially or completely;
the detected at least one first reflection (14; 16; 16a; 16b; 16c; 16d; 16e; 16f) occludes in the first image (36a) an eyelid corner (26) of the eye (10) partially or completely;
the detected at least one first reflection (14; 16; 16a; 16b; 16c; 16d; 16e; 16f) occludes in the first image (36a) a portion of the eye (10), where the detection of a useful reflection was expected.

7. The method according to claim 1, characterized in that
if in step b) at least two first reflections (14; 16; 16a; 16b; 16c; 16d; 16e; 16f) are detected that are determined to be reflected by the eye (10) and the at least two first reflections (14; 16; 16a; 16b; 16c; 16d; 16e; 16f) are determined to comprise a distance from each other that is smaller than a predetermined value, the light sources (34) that have emitted the light that causes the at least two reflections (14; 16; 16a; 16b; 16c; 16d; 16e; 16f) are determined and the intensity of at least one of the determined light sources (34) is changed, especially switched off.

8. The method according to claim 1, characterized in that
the detected at least one first reflection (14; 16; 16a; 16b; 16c; 16d; 16e; 16f) fulfils the definition of a useful reflection if it is not determined and/or categorized as disruptive reflection.

9. The method according to claim 1, characterized in that
the detected at least one first reflection (14; 16; 16a; 16b; 16c; 16d; 16e; 16f) fulfils the definition of a useful reflection if it is not determined and/or categorized as disruptive reflection and fulfils at least one of the third criteria:
the detected at least one first reflection (14; 16; 16a; 16b; 16c; 16d; 16e; 16f) is a glint or a Purkinje image, especially a reflection from an outer surface of a cornea of the eye (10) and/or from an inner surface of a cornea of the eye (10) and/or from an anterior surface of a lens of the eye (10) and/or from a posterior surface of a lens of the eye (10);
the detected at least one first reflection (14; 16; 16a; 16b; 16c; 16d; 16e; 16f) is reflected by a sclera (22) of the eye (10);
the detected at least one first reflection (14; 16; 16a; 16b; 16c; 16d; 16e; 16f) is reflected by an eyelid (24) of the eye (10);
the detected at least one first reflection (14; 16; 16a; 16b; 16c; 16d; 16e; 16f) is reflected by a face portion of the user different from the eye (10) and eyelid (24), especially a face portion within a maximum distance from the eye (10);
the detected at least one first reflection (14; 16; 16a; 16b; 16c; 16d; 16e; 16f) is reflected by a front surface and/or a back surface of glasses (12a) of spectacles (12) worn by the user.

10. The method according to claim 9, characterized in that
during processing the first image (36a) the processing unit checks for at least one of the third criteria.

11. The method according to claim 1, characterized in that
in step e) the plurality of light sources (34) is controlled to remove the at least one first reflection (14; 16; 16a; 16b; 16c; 16d; 16e; 16f) if it fulfils the predetermined definition of a disruptive reflection and/or to produce at least one second reflection in a captured second image (36b) that fulfils the predetermined definition of a useful reflection.

12. The method according to claim 1, characterized in that
if the detected at least one first reflection (14; 16; 16a; 16b; 16c; 16d; 16e; 16f) neither fulfils the definition of a disruptive reflection nor the definition of a useful reflection it is categorized as neutral reflection and is assigned to a third reflection category.

13. The method according to claim 12,
characterized in that
the light source (34) is determined by analyzing the first image (36*a*), especially on the basis of the position of the detected at least one first reflection (14; 16; 16*a*; 16*b*; 16*c*; 16*d*; 16*e*; 16*f*).

14. The method according to claim 12,
characterized in that
the light source (34) is determined by using a model of the eye (10) and/or a model of a face of the user and/or a model of spectacles (12) worn by the user and/or given positions of the light sources (34) and/or a given position of the imaging device (32).

15. The method according to claim 1,
characterized in that
if the detected at least one first reflection (14; 16; 16*a*; 16*b*; 16*c*; 16*d*; 16*e*; 16*f*) is categorized as a disruptive reflection or a neutral reflection, at least one light source (34) of the plurality of light sources (34) is determined as having emitted the light that causes the disruptive reflection or neutral reflection and a light intensity of the at least one determined light source (34) is reduced or especially the at least one determined light source (34) is switched off for capturing a second image (36*b*).

16. The method according to claim 1,
characterized in that
if the detected at least one first reflection (14; 16; 16*a*; 16*b*; 16*c*; 16*d*; 16*e*; 16*f*) is categorized as a useful reflection and the predefined quality criterion is not satisfied, at least one quality feature is derived from the first image (36*a*) and at least one light source (34) of the plurality of light sources (34) is determined as having emitted the light that causes the useful reflection and a light intensity of the at least one determined light source (34) is changed in dependency of the derived quality feature for capturing a second image (36*b*).

17. The method according to claim 16,
characterized in that
the light source (34) to be expected to produce a useful reflection is determined on the basis of a position of the light source (34) having been determined to emit the light causing the detected at least one first reflection (14; 16; 16*a*; 16*b*; 16*c*; 16*d*; 16*e*; 16*f*).

18. The method according to claim 1,
characterized in that
at least one inactive light source (34) of the plurality of light sources (34) is determined to produce a useful reflection, especially a reflection reflected by the inner and/or outer surface of the cornea, and the determined light source (34) is switched on for capturing a second image.

19. The method according to claim 1,
characterized in that
the method comprises the step:
f) one light source (34) of the plurality of light sources (34) is switched on and a second image (36*b*) is captured, wherein the second image (36*b*) is compared to the first image (36*a*) and if a second reflection in the second image (36*b*) is determined on a second position that was not present in the first image (36*a*), the one light source (34) is determined of having emitted the light causing the second reflection.

20. The method according to claim 1,
characterized in that
the method comprises the step:
g) one light source (34) of the plurality of light sources (34), which has emitted light during capturing the at least one first image (36*a*), is switched off for capturing a second image (36*b*), the second image (36*b*) is captured and compared to the first image (36*a*) and if a reflection in the second image (36*b*) has disappeared compared to the first image (36*a*), the one light source (34) is determined of having emitted the light that caused in the first image (36*a*) the reflection that has disappeared in the second image (36*b*).

21. The method according to claim 1,
characterized in that
step f) and/or step g) is repeated for a sequence of subsequent captured images (36*a*; 36*b*) until it has been fully determined which light source (34) produced which reflection (14; 16; 16*a*; 16*b*; 16*c*; 16*d*; 16*e*; 16*f*).

22. The method according to claim 1,
characterized in that
each of the light sources (34) has a specific characteristic different from each other, wherein the characteristic is provided by each of the light sources (34) emitting light with a specific wavelength spectrum and/or the characteristic is provided by each of the light sources (34) configured to emit light out of an emitting region having a distinctive shape each, wherein the distinctive shapes of each light source (34) differ from each other, wherein the processing unit uses the specific characteristic to determine the light source (34) having emitted the detected at least one first reflection (14; 16; 16*a*; 16*b*; 16*c*; 16*d*; 16*e*; 16*f*).

23. The method according to claim 1,
characterized in that
if at least two reflections (16; 16*a*; 16*b*; 16*c*; 16*d*; 16*e*; 16*f*) are detected as being reflected by glasses (12*a*) worn by the user, a position of the glasses (12*a*) relative to the face of the user is determined on the basis of the at least two detected reflections (16; 16*a*; 16*b*; 16*c*; 16*d*; 16*e*; 16*f*) and their determined positions.

24. The method according to claim 1,
characterized in that
if the detected at least one first reflection (14; 16; 16*a*; 16*b*; 16*c*; 16*d*; 16*e*; 16*f*) is determined to be reflected from glasses (12*a*) worn by a user, a characteristic of the glasses (12*a*), especially a refractive power of the glasses (12*a*), is determined on the basis of the position of the at least one first reflection (14; 16; 16*a*; 16*b*; 16*c*; 16*d*; 16*e*; 16*f*).

25. The method according to claim 24,
characterized in that
the determined characteristic of the glasses (12*a*) is used to determine the at least one property of the user's eye (10).

26. The method according to claim 1,
characterized in that
from the first image (36*a*) a position of the eye (10) in the first image (36*a*) is determined, the position of the detected at least one first reflection (14; 16; 16*a*; 16*b*; 16*c*) is determined relative to the position of the eye (10) and/or a light source (34) of the plurality of light sources (34) that causes the reflection is determined on the basis of the position of the eye (10) and an eye (10) model and/or a light source (34) of the plurality of light sources (34) is determined to be expected to produce a useful or disruptive or neutral reflection on the basis of the position of the eye (10) and an eye model and additionally on the basis of the positions of the light sources (34) and the position of the imaging device (32).

27. The method according to claim 1,
characterized in that
a light source (34) of the plurality of light sources (34) is determined to produce and/or to be expected to produce a disruptive or useful or neutral reflection by processing an input signal provided by an accelerometer and/or magnetometer and/or attitude sensor that determines a spatial orientation of the eye tracking device (30) with respect to the user's head and/or eye (10).

28. The method according to claim 1,
characterized in that
the imaging device (32) captures a second image while the at least one light source (34) of the plurality of light sources (34) emits light, the processing unit compares the first and the second image and if in the first image (36*a*) the at least one first reflection (14; 16; 16*a*; 16*b*; 16*c*; 16*d*; 16*e*; 16*f*) was detected as a useful reflection and in the second image is no reflection in the determined position of the at least one first reflection (14; 16; 16*a*; 16*b*; 16*c*; 16*d*; 16*e*; 16*f*) is detected, a light source (34) is determined that is expected to produce a useful reflection on the basis of the detected useful reflection in the first image (36*a*) and the determined light source (34) is switched on for capturing a third image.

29. Eye tracking device for capturing at least one property of at least one eye (10) of a user, wherein the eye tracking device (30) comprises at least one imaging device (32) capable of capturing images (36*a*; 36*b*) of the at least one eye (10) of the user, a plurality of light sources (34) capable of illuminating the at least one eye (10) of the user, a processing unit capable of processing images (36*a*; 36*b*) captured by the imaging device (32) and a control unit capable of controlling the plurality of light sources (34) in their light intensity separately, wherein
  a) the imaging device (32) is capable of capturing a first image (36*a*) while at least one of the light sources (34) emits light; and
  b) the processing unit is capable of processing the first image (36*a*) and by processing the first image (36*a*) determining whether reflections are detected in the first image (36*a*);
characterized in that
  c) if at least one first reflection (14; 16; 16*a*; 16*b*; 16*c*; 16*d*; 16*e*; 16*f*) is detected, the processing unit is capable of determining a position in the first image (36*a*) of the at least one first reflection (14; 16; 16*a*; 16*b*; 16*c*; 16*d*; 16*e*; 16*f*);
  d) the processing unit is capable of categorizing the first reflection (14; 16; 16*a*; 16*b*; 16*c*) at least on the basis of the position in the first image (36*a*); and
  e) the processing unit is capable of checking whether the first image (36*a*) fulfils a predefined quality criterion and if the first image (36*a*) does not fulfil the predefined quality criterion, the control unit is capable of controlling the plurality of light sources (34) at least in dependence of the categorization by changing the light intensity of at least one light source (34) of the plurality of light sources (34).

\* \* \* \* \*